United States Patent [19]
Lonial et al.

[11] Patent Number: 6,001,560
[45] Date of Patent: Dec. 14, 1999

[54] HUMAN GAMMA INTERFERON ANTAGONIST/AGONIST SCREEN

[75] Inventors: Herinder K. Lonial, Congers, N.Y.; Satwant K. Narula, West Caldwell; Paul J. Zavodny, Mountainside, both of N.J.

[73] Assignee: Schering Corporation, Kenilworth, N.J.

[21] Appl. No.: 07/959,509

[22] Filed: Oct. 9, 1992

Related U.S. Application Data

[63] Continuation of application No. 07/616,621, Nov. 21, 1990, abandoned.

[51] Int. Cl.$^6$ ............................. C12Q 1/68; C07H 21/09
[52] U.S. Cl. .......................... 435/6; 435/69.1; 435/320.1; 435/252.3
[58] Field of Search ..................... 435/6, 69.1, 320.1, 435/252.3; 536/27; 935/47, 48

[56] References Cited

U.S. PATENT DOCUMENTS

| | | | |
|---|---|---|---|
| 4,727,138 | 2/1988 | Goeddel et al. | 536/27 |
| 5,223,421 | 6/1993 | Smith et al. | 435/193 |

OTHER PUBLICATIONS

Wurm et al. Biologicals 18:159–164 (1990).
MacDonald Critical Reviews in Biotechnology 10(2):155–178 (1990).
(4AR) Tsang et al. Mol. & Cell Biol. 10(2):711 (1990).
(3AT) Tsang et al. P.N.A.S. 85:8598 (1988).
Selden et al. Mol. and Cell Biol. 6(9):3173 (1986).
Blanai et al. P.N.A.S. 85:4672 (1988).
Sugimoto et al. Cancer Res. 49:1824 (1989).
Koeffler et al. P.N.A.S. 81:4080 (1984).
Rosa et al. J. of Immunol.140(5):1660 (1988).
Basta et al., J. Immunol. 138:1275 (1987).
Basta et al., Proc. Natl. Acad. Sci. USA 85:8618 (1988).
Das et al., Proc. Natl. Acad. Sci. USA 80:3543 (1983).
Dorn et al., Proc. Natl. Acad. Sci. USA 84:6249 (1987).
Miwa et al., Proc. Natl. Acad. Sci. USA 84:4939 (1987).
Selden et al., Mol. Cell Biol. 6:3173 (1986).
Sherman et al., Proc. Natl. Acad. Sci. USA 84:4254 (1987).
Sherman et al., Mol. Cell. Biol. 9:50 (1989).
Tsang et al., Proc. Natl. Acad. Sci. USA 85:8598 (1988).
Tsang et al., Mol. Cell. Biol. 10:711 (1990).

*Primary Examiner*—Kenneth R. Horlick
*Attorney, Agent, or Firm*—Immac J. Thampoe

[57] ABSTRACT

Stably-transformed human cell lines containing a human gamma interferon-responsive human HLA-DRα promoter operatively linked to a reporter gene are provided. Also provided are methods for using such transformed cell lines to screen for agonists and/or antagonists of human gamma interferon.

17 Claims, 3 Drawing Sheets

SEQUENCE LISTING (1) GENERAL INFORMATION:

(iii) NUMBER OF SEQUENCES:  4

(2) INFORMATION FOR SEQ ID NO: 1:

(i) SEQUENCE CHARACTERISTICS:
      (A) LENGTH:   27 base pairs
      (B) TYPE:   nucleic acid
      (C) STRANDEDNESS:   single
      (D) TOPOLOGY:   linear (xi) SEQUENCE DESCRIPTION: SEQ ID NO: 1:

AGCTAAGCTT TATCCAATGA ACGGAGT                           27

(2) INFORMATION FOR SEQ ID NO: 2:

(i) SEQUENCE CHARACTERISTICS:
      (A) LENGTH:   30 base pairs
      (B) TYPE:   nucleic acid
      (C) STRANDEDNESS:   single
      (D) TOPOLOGY:   linear (xi) SEQUENCE DESCRIPTION: SEQ ID NO: 2:

GACTAAGCTT GAGCTCGGGA GTGAGGCAGA                      30

(2) INFORMATION FOR SEQ ID NO: 3:

(i) SEQUENCE CHARACTERISTICS:
      (A) LENGTH:   195 base pairs
      (B) TYPE:   nucleic acid
      (C) STRANDEDNESS:   double
      (D) TOPOLOGY:   linear (xi) SEQUENCE DESCRIPTION: SEQ ID NO: 3:

CTTTATCCAA TGAACGGAGT ATCTTGTGTC CTGGACCCTT TGCAAGAACC      50

CTTCCCCTAG CAACAGATGC GTCATCTCAA AATATTTTTC TGATTGGCCA     100

AAGAGTAATT GATTTGCATT TTAATGGTCA GACTCTATTA CACCCCACAT     150

TCTCTTTTCT TTTATTCTTG TCTGTTCTGC CTCACTCCCG AGCTC          195

(2) INFORMATION FOR SEQ ID NO: 4:

(i) SEQUENCE CHARACTERISTICS:
      (A) LENGTH:   1196 base pairs
      (B) TYPE:   nucleic acid
      (C) STRANDEDNESS:   double (D) TOPOLOGY: linear (xi) SEQUENCE DESCRIPTION: SEQ ID NO: 4:

| | | | | | |
|---|---|---|---|---|---|
| AGATCTTTAA | TAATCATATG | ACAAGAGAAA | AACTTTCATA | ATCTTATGAC | 50 |
| ATGAGGGAAG | GAATATTAAA | GCCGTTCTGT | GAGTTATTAT | CTCTAACGTT | 100 |
| CCCAATAGAA | TAGGCTTTGC | CAGCTGGGTG | CGGTGGCTCA | TGCCTGTAAT | 150 |
| CCCAGCACTT | TGCGAGGCCA | AGGCGGGCAA | ATCACGAGGT | CAGGAGTCTG | 200 |
| AGACCAGCCT | GACCAACATG | GTGAAACCCC | GTCTCTACTA | AAAATACAAA | 250 |
| AATTAGCCGG | GAGGCCGAGA | TTACAATGAG | CTGAGATCAC | ACCACCAACT | 300 |
| CCAGCTTGGG | CGACAGAGCA | AGACTCTGTC | AAAAAAAAAA | AAAAAAAAAA | 350 |
| GAATAGGCTT | TGCCACTATA | CTCTCTCATA | TTCATTGACC | TTGAATCCTC | 400 |
| AAATGAGGTG | TGTCCATTAG | TCAACTCCAA | TCTCTTGTCA | TATATAAGAT | 450 |
| GGTAGAGATG | AGAAGAAGGT | AGCTCCTTTA | CAGCCCACTA | TTTCCACTAA | 500 |
| CTACTACCTG | TGTTTCAAGA | TACAGCCTTT | CACCTCCTTC | TCCAGTGTTG | 550 |
| AGAGTGTTGA | ACCTCAGAGT | TTCTCCTCTC | ATTTTCTCTA | AATGAGATAC | 600 |
| AATGCCAGCC | ATCCCAAGCT | CTTGGCCTGA | GTTGATCATC | TTCAAGTCTA | 650 |
| GGACTCCAAG | AAGCATGAAA | AGAGCTTCTT | TAGTGAAGCT | ATGTCCTCAG | 700 |
| TACTGCCAAA | ATTCAGACAA | TCTCCATGGC | CTGACAATTT | ACCTTCTATT | 750 |
| TGGGTAATTT | ATTGTCCCTT | ACGCAAACTC | TCCAACTGTC | ATTGCACAGA | 800 |
| CATATGATCT | GTATTTAGCT | CTCACTTTAG | GTGTTTCCAT | CGATTCTATT | 850 |
| CTCACTAATG | TGCTTCAGGT | ATATCCCTGT | CTAGAAGTCA | GATTGGGGTT | 900 |
| AAAGAGTCTG | CCGTGATTGA | CTAACAGTCT | TAAATACTTG | ATTTGTTGTT | 950 |
| GTTGTTGTCC | TGTTTGTTTA | AGAAACTTTA | CTTCTTTATC | CAATGAACGG | 1000 |
| AGTATCTTGT | GTCCTGGACC | CTTTGCAAGA | ACCCTTCCCC | TAGCAACAGA | 1050 |
| TGCGTCATCT | CAAAATATTT | TTCTGATTGG | CCAAAGAGTA | ATTGATTTGC | 1100 |
| ATTTTAATGG | TCAGACTCTA | TTACACCCCA | CATTCTCTTT | TCTTTTATTC | 1150 |
| TTGTCTGTTC | TGCCTCACTC | CCGAGCTCTA | CTGACTCCCA | AAAGAG | 1196 |

HUMAN GAMMA INTERFERON ANTAGONIST/AGONIST SCREEN

This is a continuation, application Ser. No. 07/616,621 filed Nov. 21, 1990, abandoned.

TECHNICAL FIELD

This invention relates to stably-transformed human cell lines containing a human gamma interferon-responsive human HLA-DRα promoter linked to a reporter gene, and to methods for the use of such transformed cell lines to identify agonists and/or antagonists of human gamma interferon.

BACKGROUND OF THE INVENTION

Gamma interferon (IFN-γ) is a cytokine produced by activated helper T cells, one of the most characteristic activities of which is the upregulation of MHC class IIgene expression. Class II genes (HLA-DR, -DP and -DQ) of the human major histocompatibility complex encode polymorphic cell surface glycoproteins that are expressed in specific cells of the immune system, such as B lymphocytes, macrophages, monocytes and activated T lymphocytes.

The class IIgene products are essential for cellular interactions involved in the immune response, including antigen presentation to helper T cells. It has been shown that, in addition to other biological functions, IFN-γ plays a modulatory role in antigen presentation by increasing the level of class IIgene transcription in class II-positive cells as well as inducing its expression in the otherwise class II-negative cells, which include epithelial cells, fibroblasts, endothelial cells and astrocytes [Taylor et al., Virus Res. 15:1 (1990)].

Abnormal levels or aberrant expression of class II gene products have been implicated in the onset of several autoimmune diseases such as experimental autoimmune encephalomyelitis [Massa et al., Proc. Natl. Acad. Sci. USA 84:4219 (1987)]. Interestingly, a neutralizing antibody to IFN-γ has been shown to abrogate the effects of autoimmune disease in the (NZB×NZW) F1 mouse model system of systemic lupus erythematosus [Jacob et al., J. Exp. Med. 166:798 (1987)].

Induction of class IIgene expression by IFN-γ is regulated in part at the transcriptional level [Basta et al., Proc. Natl. Acad. Sci. USA 85:8618 (1988); Blanar et al., Proc. Nat). Acad. Sci. USA 85:4672 (1988)]. Functional studies have focused on identifying the cis-acting elements that are important for regulated class II gene expression.

Chimaeric DNA constructs containing 5' promoter deletions of the HLA-DRα gene linked to a reporter gene such as the bacterial chloramphenicol acetyltransferase (CAT) gene have been transiently transfected into several types of cells. From these studies, sequences that are important for IFN-γ-induced expression in glioblastoma cells have been identified [Basta et al., J. Immunol. 138:1275 (1987); Basta et al., supra], as well as regions important for constitutive expression in lymphoblastoid cells and inducible expression in HeLa cells [Sherman et al., Proc. Natl. Acad. Sci. USA 84:4254 (1987); Tsang et al., Proc. Natl. Acad. Sci. USA 85:8598 (1988); Sherman et al., Mol. Cell. Biol. 9:50 (1989); Tsang et al., Mol. Cell. Biol. 10:711 (1990)].

Within the regions that have been identified as functionally important, highly-conserved sequences designated as X, Y, Z/W-boxes and an octamer (O) binding site have been noted [Miwa et al., Proc. Natl. Acad. Sci. USA 84:4939 (1987); Dorn et al., Proc. Natl. Acad. Sci. USA 84:6249 (1987); Sherman et al., Mol. Cell. Biol. 9:50 (1989); Tsang et al., Mol. Cell. Biol. 10:711 (1990)]. Mutational studies have suggested the functional importance of these elements.

For example, all four elements (X, Y, Z and O) are necessary for B cell specificity, whereas only the X, Y, and Z boxes are required for IFN-γ inducibility. In addition, the Z box and sequences flanking the Z and X boxes appear to help in establishing low levels of expression in T cells and uninduced cells.

X-box binding is defective in cells from patients with the combined immunodeficiency syndrome, a hereditary disease characterized by the absence of class II expression in all tissues [Reith et al., Cell 53:897 (1988); Sherman et al., Mol. Cell. Biol. 9:50 (1989); Tsang et al., Mol. Cell. Biol. 10:711 (1990)].

The cloning of some of the DNA-binding proteins including those recognizing the X and Y boxes has been achieved, but their presence does not appear to correlate precisely with IFN-γ-induced expression [Liou et al., Science 242:69 (1988); Celada et al., Mol. Cell. Biol. 9:3097 (1989); Reith et al., Proc. Natl. Acad. Sci. USA 86:4200 (1989)].

Because of its involvement in autoimmune disorders, there is impetus for the development of agents that can antagonize the effects of IFN-γ. Yet, it has long been known that such interferon also has beneficial antiviral and antiproliferative activities that are useful in the treatment of neoplastic and viral diseases. For that reason, efforts are also being made to find agonists of IFN-γ.

The search for such agonists and antagonists would be facilitated by the development of a fast and effective in vitro screening system.

SUMMARY OF THE INVENTION

The present invention fills this need by providing materials and methods for such screening.

More particularly, this invention provides human cell lines which have been stably transformed by recombinant vectors comprising a reporter gene operatively linked to a promoter that has a nucleotide sequence corresponding to the sequence of a human HLA-DRα gene and is delimited at the 5' end by a nucleotide residue corresponding to one of residues −1300 to −136 and at the 3' end by a residue corresponding to about residue +32, both delimiting nucleotide residues being numbered from the site of transcription initiation of the human HLA-DRα gene, expression of which reporter gene can be induced at least 10 fold (preferably 80 fold) by human IFN-γ.

This invention further provides methods for detecting human IFN-γ agonists in samples comprising:

(a) providing a human cell line which has been stably transformed by a recombinant vector comprising a reporter gene operatively linked to a promoter that has a nucleotide sequence corresponding to the sequence of a human HLA-DRα gene and is delimited at the 5' end by a residue corresponding to one of residues −1300 to −136 and at the 3' end by a residue corresponding to about residue +32, both delimiting nucleotide residues being numbered from the site of transcription initiation of the human HLA-DRα gene, expression of which reporter gene can be induced by human IFN-γ;

(b) contacting the transformed cell line with a sample suspected to contain a human IFN-γ agonist, under conditions in which human IFN-γ would cause increased expression of the reporter gene; and (c) measuring the level of expression of the reporter gene, whereby the presence of a human IFN-γ agonist in the sample is detected by measurement of an increased level of expression of the reporter gene, compared to the level produced by a buffer control.

This invention still further provides methods for detecting human IFN-γ antagonists in samples comprising:

(a) providing a human cell line which has been stably transformed by a recombinant vector comprising a reporter gene operatively linked to a promoter that has a nucleotide sequence corresponding to the sequence of a human HLA-DRα gene and is delimited at the 5' end by a nucleotide residue corresponding to one of residues −1300 to −136 and at the 3' end by a residue corresponding to about residue +32, both delimiting nucleotide residues being numbered from the site of transcription initiation of the human HLA-DRα gene, expression of which reporter gene can be induced by human IFN-γ;

(b) contacting the transformed cell line with a sample suspected to contain a human IFN-γ antagonist, to which has been added an amount of human IFN-γ that, absent such antagonist, would produce a measurable increase in expression of the reporter gene; and (c) measuring the level of expression of the reporter gene, whereby the presence of a human IFN-γ antagonist in the sample is detected by measurement of a decreased level of expression of the reporter gene, compared to the level produced by the human IFN-γ in the absence of such antagonist.

BRIEF DESCRIPTION OF THE FIGURES

This invention can be more readily understood by reference to the accompanying figures, in which.

Results from the radioimmunoassay of growth hormone (cpm) are shown as a function of IFN-γ concentration for the indicated cell lines. Transformed cell lines that were unresponsive to IFN-γ and constitutive growth hormone expressors are designated HL303 and HL306, respectively. The line designated Hela was not transformed with the plasmid. Within each set, the bars from left to right represent results obtained with 0, 1, 5 and 10 units, respectively, of IFN-γ.

Figure 3:
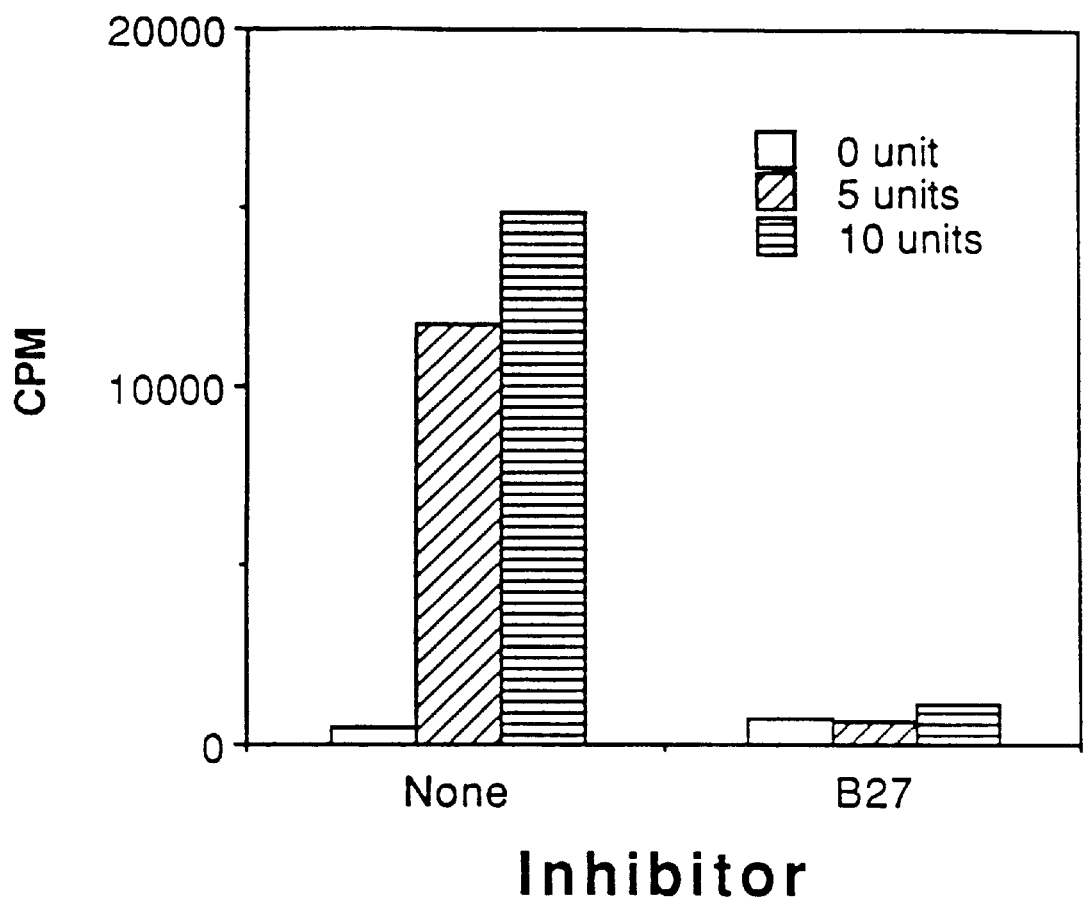

FIG. 3 is a graphical representation of the effects of a neutralizing anti-IFN-γ monoclonal antibody on the induction of human growth hormone synthesis by varying levels of human IFN-γ in a HeLa cell line stably transformed with plasmid pHL-cII-hGH. Results from the radioimmunoassay of growth hormone (cpm) are shown as a function of IFN-γ concentration, both with (B27) and without (None) the antibody. Within each set, the bars from left to right represent results obtained with 0, 5 and 10 units, respectively, of IFN-γ.

Because the methods of this invention target class II gene expression, they may be used to identify IFN-γ agonists/antagonists that are specific for this biological function and that do not affect other functions. The methods also, however, permit the identification of agents which affect the binding of human IFN-γ to its cellular receptors.

Description of the Invention

All references cited herein are hereby incorporated in their entirety by reference. All nucleic acid sequences disclosed follow the normal 5' to 3' convention, as read from left to right. Standard single-letter abbreviations are used for the nucleotide bases in the sequences (37 C.F.R. §1.822).

As used herein, the term "agonist" is defined as a substance that, like human IFN-γ, stimulates (induces) expression of a gene operatively linked to the HLA-DRα genomic promoter element. The term "antagonist" is defined as a substance that blocks or inhibits such stimulatory activity by gamma interferon.

A "reporter gene" can be either a DNA molecule isolated from genomic DNA, which may or may not contain introns, or a complementary DNA (cDNA) prepared using messenger RNA as a template. In either case, the DNA encodes an expression product that is readily measurable, e.g., by biological activity assay, enzyme-linked immunosorbent assay (ELISA) or radioimmunoassay (RIA).

The term "DNA fragment" means a DNA molecule, the nucleic acid sequence of which corresponds to the sequence of a subsequence of the human HLA-DRα gene. Such fragments can be produced by enzymatic cleavage of genomic DNA. They are not limited, however, to the products of such cleavage but include subsequences, the termini of which do not correspond to any enzymatic cleavage points. These fragments can be made, e.g., by chemical synthesis or by use of the polymerase chain reaction (PCR).

As used herein, human "gamma interferon" means a protein which (a) has an amino acid sequence substantially identical to the sequence of mature human IFN-γ disclosed by Goeddel et al. in U.S. Pat. No. 4,727,138 and (b) has biological activity that is common to native IFN-γ. Substantial identity of amino acid sequences means that the sequence of another IFN-γ compared to the sequence disclosed by Goeddel et al. is identical or differs by one or more amino acid alterations (deletions, additions, substitutions) that do not substantially impair biological activity.

For example, IFN-γ D, which lacks the first three amino-terminal residues, and IFN-γ E, a derivative lacking both the first three amino-terminal residues and the last nine carboxyl-terminal residues of the interferon described by Goeddel et al. are substantially identical in the context of this invention. So too are the natural human IFN-γs which lack the three amino-terminal residues and, in addition, display microheterogeneity at the carboxyl terminus [Seelig et al., Biochemistry 27:1981 (1988)].

The present invention provides human cell lines which have been stably transformed by recombinant vectors containing specific regions of the human HLA-DRα gene operatively linked to reporter genes. The specific regions of the human HLA-DRα gene that can be used in this invention encompass residues −1300 to about +32 of the complete gene, with the first base of the transcription initiation site of the gene being used as a point of reference and designated +1.

Figure 2:
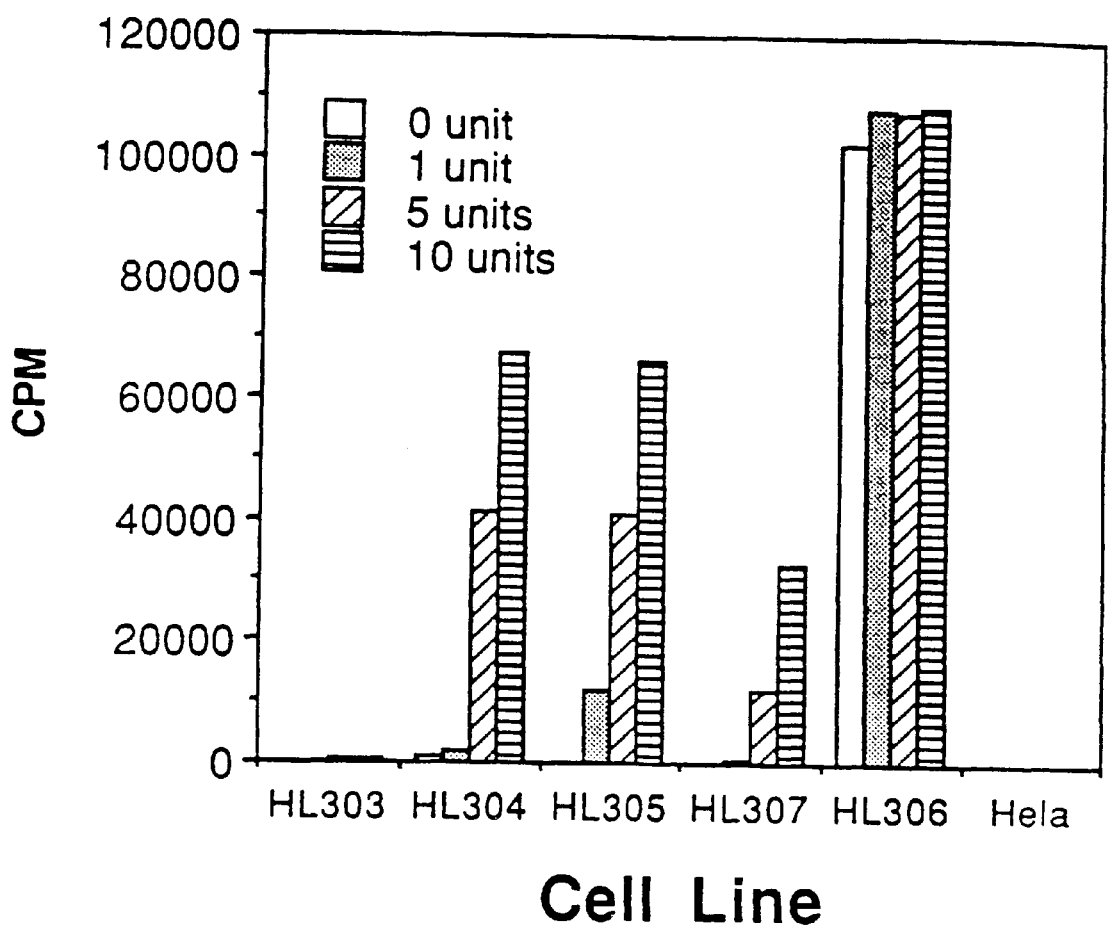
FIG. 2 is a graphical representation of the induction of human growth hormone synthesis by varying levels of human IFN-γ in various HeLa cell lines that had been stably transformed with plasmid pHL-cII-hGH.

Most of the human HLA-DRα gene nucleic acid sequence has been disclosed in FIG. 2 of a paper by Das et al. [Proc. Natl. Acad. Sci. USA 80:3547 (1983)]. Relevant portions of this sequence are defined in the Sequence Listing by SEQ ID NO:4, wherein the adenine residue at position 1147 is the first base of the transcription initiation site of the gene (+1), and residues 1 and 1178 are −1146 and +32, respectively, as defined herein. This numbering (and the sequence defined by SEQ ID NO:4) ignores three potential nucleotides represented by dashes following the cytosine residue at position 258 in the sequence published by Das et al. It should also be noted that there is an error in the numbering of the nucleotide residues in FIG. 2 of the reference of Das et al. The numbers of the last residues of line 8 et seq. should be increased by one to 962, 1084, 1204, etc.

The Z-box, X-box, Y-box and octamer elements of human HLA-DRα gene correspond approximately to residues 1016–1022, 1039–1052, 1073–1086 and 1095–1102, respectively, of the sequence defined by SEQ ID NO:4. All of these elements are present in all of the recombinant vectors used in this invention.

The recombinant vectors comprise DNA fragments having nucleic acid sequences corresponding to subsequences of the human HLA-DRα gene. Such DNA molecules are delimited at the 5' termini by a nucleotide residue corresponding to one of residues −1300 to −136 and at the 3' termini by a residue corresponding to about residue +32, both delimiting nucleotide residues being numbered from the site of transcription initiation of the human HLA-DRα gene. In a preferred embodiment, the DNA fragment has a sequence delimited by residues corresponding to residues −163 and +32. This sequence is defined in the Sequence Listing by SEQ ID NO:3.

DNA fragments having such nucleic acid sequences can be prepared by standard methods based upon the known sequence of the gene. For example, the fragments can be chemically synthesized using the phosphoramidite solid support method of Mafteucci et al. [J. Am. Chem. Soc. 10:3185 (1981)], the method of Yoo et al. [J. Biol. Chem. 76:17078 (1989)], or other well known methods. Alternatively, since the sequence of the gene and the site specificities of the many available restriction endonucleases are known, one skilled in the art can readily identify and isolate the gene from genomic DNA and cleave the DNA to obtain a desired sequence. The PCR method of Mullis et al. (U.S. Pat. No. 4,800,159) can also be used to obtain the same result. Primers used for PCR can also be designed to introduce appropriate new restriction sites, to facilitate incorporation into a given vector.

Any human cell line can be used as a source of genomic DNA from which the desired portions of the human HLA-DRα gene can be obtained. For example, the JAR human placental choriocarcinoma cell line (ATCC HTB 144) can be used. Human genomic libraries can also be prepared from such cell lines by standard methods if desired.

Although the human HLA-DRγ gene sequence identified by SEQ ID NO:4 extends only to residue −1146 at the 5' terminus, DNA sequences delimited by residues −1300 to +31 can be prepared as described by Tsang et al. [Proc. Natl. Acad. Sci. USA 25:8598 (1988)].

Of course, there may be allelic variants of the HLA-DRα sequences used in this invention. Furthermore, it is well within the skill of the art, e.g., by chemical synthesis or by the use of modified PCR primers or site-directed mutagenesis to modify the genomic DNA, to prepare various derivatives of the sequence defined by SEQ ID NO:4 in which there are single or multiple base substitutions which do not substantially impair the ability of the sequences to respond to IFN-γ induction in essentially the same way as the unmodified sequences. Such conservatively modified variants are within the scope of this invention.

Insertion of the human HLA-DRα gene DNA fragments into a vector is easily accomplished when the termini of both the fragments and the vector comprise the same restriction site. If this cannot be done, it may be necessary to modify the termini of the fragments and/or vector by digesting back single-stranded DNA overhangs generated by restriction endonuclease cleavage to produce blunt ends, or to achieve the same result by filling in the single-stranded termini with an appropriate DNA polymerase. Alternatively, any site desired may be produced by ligating nucleotide sequences (linkers) onto the termini. Such linkers may comprise specific oligonucleotide sequences that define desired restriction sites. The cleaved vector and the DNA fragments may also be modified if required by homopolymeric tailing.

Any of the well-known reporter genes can be operatively linked to one of the foregoing DNA fragments. Examples of suitable reporter genes include but are not limited to $E. coli\beta$-galactosidase [An et al., Mol. Cell. Biol. 2:1628 (1982)], xanthine-guanine phosphoribosyl transferase [Chu et al., Nucleic Acids Res. 13:2921 (1985)], galactokinase [Shumperli et al., Proc. Natl. Acad. Sci. USA 79:257 (1982)], interleukin-2 [Cullen, Cell 46:973 (1986)], thymidine kinase [Searle et al., Mol. Cell. Biol. 5:1480 (1985)], firefly luciferase [De Wet et al., Mol. Cell. Biol. 7:725 (1987)], alkaline phosphatase [Henthorn et al., Proc. Natl. Acad. Sci. USA 85:6342 (1988)], secreted placental alkaline phosphatase [Berger et al., Gene 66:1 (1988)] and chloramphenicol acetyltransferase (CAT) [Gorman et al., Mol. Cell. Biol. 2:1044 (1982); Tsang et al., Proc. Natl. Acad. Sci. USA 85:8598 (1988)].

The preferred reporter gene is the human growth hormone gene, the use of which is described in the Example below. Human growth hormone is secreted into the medium by human cells expressing the gene. Thus, disruption of the cells to measure the hormone is unnecessary. Although the gene used in the Example was obtained from a commercially available plasmid, one skilled in the art could instead isolate the gene by standard methods from a human cell line such as the JAR line, preferably using PCR and primers based upon the known nucleotide sequence of the gene [Denoto et al., Nucleic Acids Res. 9:3719 (1981)].

Expression products of the reporter genes can be measured using standard methods. For example, bioassays can be carried out for biologically active proteins such as interleukin-2. Enzyme assays can be performed when the reporter gene product is an enzyme such as alkaline phosphatase. Alternatively, various types of immunoassays such as competitive immunoassays, direct immunoassays and indirect immunoassays may be used.

Such immunoassays involve the formation of immune complexes containing the reporter gene product and and a measurable label. As used herein, the term "label" includes moieties that can be detected directly, such as fluorochromes and radiolabels, and moieties such as enzymes that must be reacted or derivatized to be detected.

In competitive immunoassays, samples from induced cultures (following cell disruption if the reporter gene product is not secreted) are incubated with an antibody against the reporter gene product and a known amount of labeled reporter gene product. Any unlabeled product produced by the cells competes with the labeled material for binding to the antibody. The resulting immune complexes are separated and the amount of labeled complex is determined. The reporter gene product produced by the cells can be quantified by comparing observed measurements to results obtained from standard curves.

Direct immunoassays involve incubating culture samples with a labeled antibody against the reporter gene product and separating any immune complexes that form. The amount of label in the complexes is determined and can be quantified by comparison to standard curves.

Enzyme-linked immunosorbant assays (ELISAs) can also be carried out by well known methods, e.g., as described in U.S. Pat. No. 4,665,018 to Vold.

The particular label used will depend upon the type of immunoassay used. Examples of labels that can be used include, e.g., radiolabels such as $^{32}P$, $^{125}I$, $^{3}H$ and $^{14}C$; fluorescent labels such as fluorescein and its derivatives, rhodamine and its derivatives, dansyl and umbelliferone; chemiluminescers such as luciferia and 2,3-dihydrophthalazinediones; and enzymes such as horseradish peroxidase, alkaline phosphatase, lysozyme and glucose-6-phosphate dehydrogenase.

The antibody or reporter gene product, as the case may be, can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels.

The human HLA-DRα gene DNA fragments used in this invention can be inserted into many mammalian reporter gene-containing vectors, including but not limited to plasmids pSV2Apap, pMAMneo-CAT, pMAMneo-LUC, pSVOCAT, pBCO, pBLCAT2, pBLCAT3, pON1, pCH110 and various plasmids described by De Wet et al., supra. Where a desired vector contains a different promoter, the promoter can be excised using standard methods and replaced by a human HLA-DRα gene DNA fragment promoter. In the Example below, plasmid p+e,sez O+ee GH, which lacks a eukaryotic promoter but contains the human growth hormone structural gene sequences, was used. A human HLA-DRα gene DNA fragment was simply inserted into this vector to supply the promoter function.

The foregoing recombinant vectors can be used to stably transform any human cell line that is capable of responding to human IFN-γ by induction of HLA class IIgene expression. Many such cell lines are available including, e.g., the U-373MG glioblastoma/astrocytoma (ATCC HTB 17), HUV-EC-C umbilical cord (ATCC CRL 1730), U-937 histiocytic lymphoma (ATCC CRL 1593) and HeLa cervical epitheloid carcinoma (ATCC CCL 2) cell lines.

Stable transformation of a suitable human cell line can be accomplished by using standard methods to co-transfect the cells with one of the above-mentioned recombinant vectors and with a second vector which confers resistance to a selection agent such as an antibiotic. Alternatively, transformation can be carried out with a single vector containing both the human HLA-DRα gene fragment/reporter gene component and the selection marker gene. In the Example below, co-transfection was carried out using plasmid pSV2neo, which provides a dominant selectable marker for resistance to antibiotic G418 in mammalian cells.

EXAMPLE

The present invention can be illustrated by the following, non-limiting example.

Unless otherwise specified, percentages given below for solids in solid mixtures, liquids in liquids, and solids in liquids are on a wt/wt, vol/vol and wt/vol basis, respectively.

Materials Used

Restriction enzymes and T4 DNA ligase were purchased from New England Biolabs, Beverly, Mass.; *Thermus aquaticus* (Taq) DNA polymerase was obtained from Statagene, LaJolla, Calif.; and calf intestine phosphatase was supplied by Boehringer Mannheim Biochemicals, Indianapolis, Ind. All enzymes were used in accordance with the manufacturers' instructions. The Sequenase version 2.0 sequencing system was obtained from United States Biochemical, Cleveland, Ohio.

Plasmid vector p+e,sez O+ee GH was purchased from Nichols Institute Diagnostics, San Juan Capistrano, Calif. Plasmid vector pSV2neo (ATCC 37149) and *E. coli* K12 strain MM294 (ATCC 33625) were obtained from the American Type Culture Collection, Rockville, Md.

A radioimmunoassay kit used for measuring levels of human growth hormone (hGH) was purchased from Nichols Institute Diagnostics, San Juan Capistrano, Calif., and used in accordance with the manufacturer's instructions.

Recombinant human IFN-γ E was prepared in an *E. coli* expression system and purified by standard methods. This interferon had a specific biological activity of $3.9 \times 10^8$ units/milligram, with a unit of interferon activity defined as the inverse of the fold-dilution required to produce 50% of maximum activity in a cytopathic effect reduction assay using human FS 71 cells and encephalomyocarditis virus [Yip et al., Proc. Natl. Acad. Sci. USA 78:1601 (1981)]. Recombinant IFN-γ that is adequate to demonstrate the utility of the present invention can also be purchased, e.g., from Genzyme Corporation, Boston, Mass.

A neutralizing murine anti-human-IFN-γ monoclonal antibody designated B27 was prepared using standard methods. Similar antibodies are available commercially, e.g., from Genzyme Corporation.

Tissue culture grade dexamethasone was purchased from Sigma Chemical Company, St. Louis, Mo.

Synthetic oligonucleotide primers having nucleic acid sequences as defined in the Sequence Listing by SEQ ID NO:1 (primer AB814) and SEQ ID NO:2 (primer AB816) were synthesized by standard methods using an Applied Biosystems Model 380A Synthesizer.

Cell Culture

JAR (ATCC HTB 144) and HeLa (ATCC CCL2) cell lines were obtained from the American Type Culture Collection, Rockville, Md. The JAR line, a human placental choriocarcinoma cell line, was maintained in RPMI 1640 medium supplemented with 10% heat-inactivated fetal calf serum and penicillin/streptomycin. The HeLa line, a human cervical epitheloid carcinoma cell line, was maintained in Dulbecco's Modified Eagle's Medium (DMEM) supplemented with 10% heat-inactivated fetal calf serum, 2 mM glutamine, 10 mM non-essential amino acids and 10 units/ml penicillin/streptomycin. Both cell lines were maintained in a humidified incubator with 5% $CO_2$ at 37° C.

Media and cell culture supplements, such as non-essential amino acids and penicillin/streptomycin were purchased from Gibco/BRL, Rockville, Md. Fetal calf serum was purchased from Hyclone Laboratories, Inc., Logan, Utah.

Construction of Plasmid pHL-cII-hGH

Standard recombinant DNA methods were carried out essentially as described by Maniatis et al., Molecular Cloning: A Laboratory Manual, 1982, Cold Spring Harbor Laboratory. An exemplary HLA-DRα fragment was prepared by amplifying the relevant genomic sequences from the JAR cells using PCR technology and the oligonucleotide primers AB814 (SEQ ID NO:1) and AB816 (SEQ ID NO:2). These primers span the regions −163 to −144 and +13 to +32, respectively, of the HLA-DRα gene, with +1 corresponding to the first nucleotide at the transcription initiation site. In addition to containing HLA-DRα gene sequences, each of these primers also has an incorporated kind III restriction site, to facilitate subsequent subcloning manipulations. The primers also contained random 4-nucleotide (AGCT and GACT) extensions at the 5' ends to confer protection against exonucleases and to enhance efficiency of cleavage at the Hind III sites.

PCR reactions were performed with a Techne programmable Dri-Block (GRI, Essex, UK) essentially as described by Friedman et al. [Nucleic Acids Res. 16:8718 (1988)]. Briefly, a reaction mixture consisting of 50 mM KCl, 10 mM Tris-HCl (pH 8.3), 1.5 mM $MgCl_2$, 1 mM dNTPs, 0.01% gelatin, 100 pmoles of each oligonucleotide primer, 2 ng of genomic DNA from JAR cells, and 4–8 units of Taq polymerase, was subjected to thirty 2-minute cycles of 95, 50 and 72° C., with a final extension period of 9 minutes at 72° C. At the end of the incubation, the PCR mixture was subjected to electrophoresis in a 1% agarose/Tris-borate gel. The 207 bp PCR fragment of interest was visualized by staining with ethidium bromide and purified by gel electroelution. Following gel purification, the PCR fragment was digested with Hind III.

The nucleic acid sequence of the resulting DNA fragment was as defined in the Sequence Listing by SEQ ID NO:3.

The human growth hormone gene was obtained from plasmid p+e,sez O+ee GH [Selden et al., Mol. Cell. Biol. 6:3173 (1986)] by digesting the plasmid with Hind III followed by dephosphorylation with calf intestine phosphatase. Following gel purification, the PCR fragment was ligated to the Hind III-digested plasmid p+e,sez O+ee GH at 15° C. for 22 hours in a ligation mixture consisting of 50 mM Tris-HCl (pH7.5), 10 mM $MgCl_2$, 1 mM ATP and 10 units of T4 DNA ligase.

Figure 1:
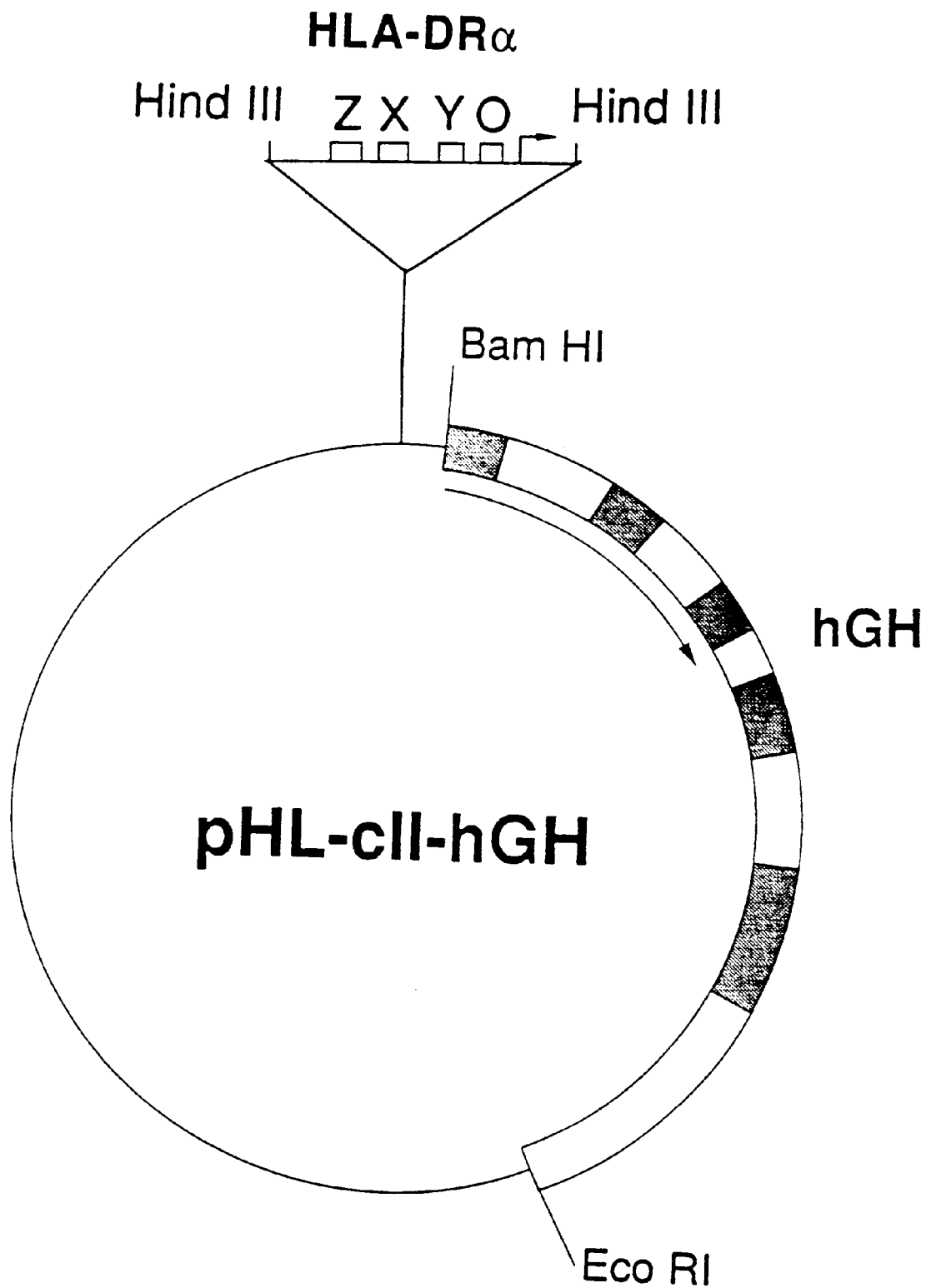
FIG. 1 is a schematic representation of plasmid pHL-cII-hGH in which shaded areas in the thick bar represent exons and clear areas represent introns and flanking sequences of the human growth hormone gene ; and Z, X and Y are conserved boxes and O is the octamer box of the HLA-DRα gene.

The ligation mixture was introduced into competent *E. coli* strain MM294 cells using the $CaCl_2$ transformation procedure (Maniatis et al., supra. page 250). Initial analysis of the transformants was done by PCR using the AB814/816 primers or by restriction digestion of partially-purified plasmid DNA with Hind III. A large-scale preparation of the desired transformant was obtained by CsCl/ethidium bromide centrifugation (Maniatis et al., supra, page 93). The authenticity of the insert was established by sequencing using the sequence version 2.0 system. The plasmid thus obtained was designated pHL-cII-hGH (FIG. 1).

Cell Transformation

HeLa cells were detached with 0.25% trypsin-EDTA and resuspended at $2\times10^7$ cells/ml in the complete medium described above. Ten μg of CsCI-purified plasmid pHL-cII-hGH DNA and 1 μg of CsCI-purified pSV2neo plasmid DNA were co-transfected into $5\times10^6$ HeLa cells by electroporation, using a Gene Pulser electroporation system (Biorad, Rockville Center, N.Y.). The transfected cells were transferred into 5 ml of complete medium in a 75 $mm^2$ tissue culture flask and incubated in a 37° C. humidified chamber with 5% $CO_2$. The medium was changed after 24 hours, and after an additional 48-hour incubation period, the transfected cells were again detached with trypsin-EDTA and plated at $5\times10^5$ cells per 100 mm culture dish in selection medium [complete HeLa medium containing 100 μg/ml G418 (Geneticin from Gibco/BRL)]. Individual G418-resistant clones were picked at day 12 post-selection and were expanded/maintained in selection medium thereafter.

In this way, a total of eleven G418-resistant clones were obtained, five of which were selected for further characterization. These clones were designated HL303–307.

IFN-γ Induction

The selected transformants described above were plated in 12-well Linbro culture dishes, with $2\times10^5$ cells in 1 ml volumes of selection medium per well. After a 4-hour incubation at 37° C. to permit cell attachment, varying doses of IFN-γ E were added in volumes of up to about 20 μl to the medium in the wells (total volume about 1 ml). The cultures were then maintained at 37° C. for an additional 48 hours, at which time radioimmunoassay for growth hormone in the culture medium was carried out.

Growth Hormone Assay

Levels of human growth hormone secreted by the various stably-transformed clones were quantified using a standard radioimmunoassay protocol employing two differentially-tagged monoclonal antibodies specific for human growth hormone. Briefly, 100-μl aliquots of the culture media from the assay wells were incubated with 100-μl volumes of a solution containing an $^{125}$I-labeled mouse monoclonal antibody and a biotin-coupled mouse monoclonal antibody which recognized a different epitope. An avidin-coated polystyrene bead was added to the reaction mixture, and the mixture was incubated for 90 minutes at room temperature, after which the beads were washed to remove unbound materials and counted in a gamma counter.

Characterization of Transformants

Stably-transformed clones HL303–HL307 were analyzed for human growth hormone production as described above, with the results shown in FIG. 2. The data in FIG. 2 were obtained following the addition of control buffer or 1, 5 or 10 units of IFN-γ E as indicated to each of the clones.

As shown in FIG. 2, clone HL303 was relatively unresponsive to the interferon and produced very low levels of growth hormone. Clone HL306 was also essentially unresponsive to the interferon but constitutively expressed high levels of growth hormone. Clones HL304, HL305 and HL307 all manifested induction by the interferon of growth hormone production, in a dose-dependent fashion. The data depicted graphically in FIG. 2 are shown numerically in the following table, where the data are expressed as counts per minute (cpm) obtained in the radioimmunoassay.

TABLE 1

Induction of Growth Hormone Synthesis of IFN-γ

| Clone | IFN-γ Added (units) | | | |
|---|---|---|---|---|
| | 0 | 1 | 5 | 10 |
| HL303 | 31 | 60 | 370 | 303 |
| HL304 | 75.4 | 2158 | 41386 | 67683 |
| HL305 | 192 | 12107 | 40597 | 66274 |
| HL307 | 36 | 286 | 12049 | 32660 |
| HL306 | 102249 | 108089 | 107337 | 108398 |
| HeLa* | 0 | 10 | 0 | 0 |

*HeLa indicates untransformed cells.

Calculations based upon the data of Table 1 show that the maximal IFN-γ induction of growth hormone synthesis in clones HL303, 304, 305 and 30 7 was 9.77, 89.76, 345.18 and 907.22 fold, respectively, compared to the level of synthesis in the absence of interferon. Because the specific biological activity of the interferon used was $3.9\times10^8$ units/mg, the 1, 5 and 10 units doses contained only 5, 25 and 50 picograms of IFN-γ protein, respectively.

Detection of IFN-γ Antagonists

To demonstrate the use of a stably transformed cell line of the invention in a screening assay for an IFN-γ antagonist, an interferon induction assay was carried out essentially as described above using HL307 cells and control buffer or 5 or 10 units of IFN-γ E, except that in some cases 5 mg/ml of monoclonal antibody B27 was added concurrently with the interferon, and the culture medium was assayed 24 hours after the addition of the interferon.

The results are shown in FIG. 3, where it can be seen that although IFN-γ E alone produced the expected degree of induction of growth hormone synthesis (3 bars on left), the antibody completely abolished induction by the interferon and reduced maximal uninhibited synthesis by about 90%.

As further confirmation of the utility of the system for the detection of interferon antagonists, a similar assay was carried out but with and without the concurrent addition of $10^{-5}$ M dexamethasone, instead of the antibody. Dexamethasone is a glucocorticoid that is known to interfere with the induction of class II surface antigen by IFN-γ, and indeed this antagonistic activity was confirmed by the assay. The presence of dexamethasone reduced IFN-γ E induction of growth hormone synthesis by the HL307 cells by about 40–50%. This degree of inhibition is about the same as the degree to which dexamethasone inhibits class II mRNA expression [Fertsch et al., J. Immunol. 139:244 (1987)] and surface antigen expression [Warren et al., J Immunol. 134:2462 (1985); Manyak et al., J. Immunol. 140:3817 (1988)] in IFN-γ-responsive cells in vitro.

Many modifications and variations of this invention can be made without departing from its spirit and scope, as will become apparent to those skilled in the art. The specific embodiments described herein are offered by way of example only, and the invention is to be limited only by the terms of the appended claims.

What is claimed is:

1. A human cell line which has been stably transformed by a recombinant vector comprising a reporter gene operatively linked to a promoter that has a nucleotide sequence corresponding to the sequence of a human HLA-DRα gene and is delimited at the 5' end by a nucleotide residue corresponding to one of residues −1300 to −136 and at the 3' end by a residue corresponding to about residue +32, both delimiting nucleotide residues being numbered from the site of transcription initiation of the human HLA-DRα gene, expression of which reporter gene can be induced by human IFNγ.

2. The cell line claim 1 in which the nucleotide sequence of the promoter is as defined in the Sequence Listing by SEQ ID NO:3.

3. The cell of line of claim 3 in which expression of the reporter gene can be induced at least 80 fold by human IFN-γ.

4. The cell line of claim 3 which is a HeLa cell line.

5. The cell line of claim 4 in which the reporter gene is a human growth hormone gene.

6. The cell line of claim 5 which has been transformed by plasmid pHL-cII-hGH.

7. A method for detecting a human IFN-γ agonist in a sample comprising:
(a) providing a human cell line which has been stably transformed by a recombinant vector comprising a reporter gene operatively linked to a promoter that has a nucleotide sequence corresponding to the sequence of a human HLA-DRα gene and is delimited at the 5' end by a nucleotide residue corresponding to one of residues −1300 to −136 and at the 3' end by a residue corresponding to about residue +32, both delimiting nucleotide residues being numbered from the site of transcription initiation of the human HLA-DRα gene, expression of which reporter gene can be induced by human IFN-γ;
(b) contacting the transformed cell line with a sample suspected to contain a human IFN-γ agonist, under conditions in which human IFN-γ would cause increased expression of the reporter gene; and
(c) measuring the level of expression of the reporter gene, whereby the presence of a human IFN-γ agonist in the sample is detected by measurement of an increased level of expression of the reporter gene, compared to the level produced by a buffer control.

8. The method of claim 7 in which the nucleotide sequence of the promoter is as defined in the Sequence Listing by SEQ ID NO:3.

9. The method of claim 7 in which the cell line is a HeLa cell line.

10. The method of claim 9 in which the reporter gene is a human growth hormone gene.

11. The method of claim 10 in which the cell line has teen transformed by plasmid pHL-cII-hGH.

12. A method for detecting a human IFN-γ antagonist in a sample comprising:

(a) providing a human cell line which has been stably transformed by a recombinant vector comprising a reporter gene operatively linked to a promoter that has a nucleotide sequence corresponding to the sequence of a human HLA-DRα gene and is delimited at the 5' end by a nucleotide residue corresponding to one of residues −1300 to −136 and at the 3' end by a residue corresponding to about residue +32, both delimiting nucleotide residues being numbered from the site of transcription initiation of the human HLA-DRαgene, expression of which reporter gene can be induced by human IFN-γ;

(b) contacting the transformed cell line with a sample suspected to contain a human IFN-γ antagonist, to which has been added an amount of human IFN-γ that, absent such antagonist, would produce a measurable increase in expression of the reporter gene; and (c) measuring the level of expression of the reporter gene, whereby the presence of a human IFN-γ antagonist in the sample is detected by measurement of a decreased level of expression of the reporter gene, compared to the level produced by the human IFN-γ in the absence of such antagonist.

13. The method of claim 12 in which the nucleotide sequence of the promoter is as defined in the Sequence Listing by SEQ ID NO:3.

14. The method of claim 12 in which the cell line is a HeLa cell line.

15. The method of claim 14 in which the reporter gene is a human growth hormone gene.

16. The method claim 15 in which the cell line has been transformed by plasmid pHL-cII-hGH.

17. Plasmid pHL-cII-hGH.

* * * * *